(12) United States Patent
Trushkowsky et al.

(10) Patent No.: US 6,511,321 B1
(45) Date of Patent: Jan. 28, 2003

(54) DENTAL ADAPTOR DEVICE

(75) Inventors: Richard Trushkowsky, Morganville, NJ (US); Joshua Friedman, Ridgefield, CT (US)

(73) Assignee: Ad Dent Inc., Danbury, CT (US)

( * ) Notice: Subject to any disclaimer, the term of this patent is extended or adjusted under 35 U.S.C. 154(b) by 0 days.

(21) Appl. No.: 09/716,804

(22) Filed: Nov. 20, 2000

Related U.S. Application Data

(63) Continuation-in-part of application No. 09/453,046, filed on Dec. 2, 1999, now Pat. No. 6,186,786.

(51) Int. Cl.[7] .................................................. A61C 3/08
(52) U.S. Cl. ........................................... 433/164; 433/29
(58) Field of Search .......................... 433/164, 29, 141, 433/142, 147, 75, 72

(56) References Cited

U.S. PATENT DOCUMENTS

| | | | | |
|---|---|---|---|---|
| 4,666,406 A | | 5/1987 | Kanca | ........................ 433/229 |
| 4,904,185 A | * | 2/1990 | McSpadden | ................. 433/164 |
| 5,030,093 A | * | 7/1991 | Mitnick | ....................... 433/164 |
| 5,098,292 A | * | 3/1992 | Lazarof | ........................ 433/141 |
| 5,681,163 A | * | 10/1997 | Wolk | .............................. 433/3 |
| 5,791,898 A | | 8/1998 | Maissami | .................... 433/164 |
| 5,797,740 A | * | 8/1998 | Lundvik | ....................... 433/29 |
| 6,208,788 B1 | * | 3/2001 | Nosov | ......................... 385/121 |

FOREIGN PATENT DOCUMENTS

| | | |
|---|---|---|
| DE | 41 33 109 C1 | 2/1993 |
| EP | 0 801 932 A1 | 10/1997 |

* cited by examiner

*Primary Examiner*—Nicholas D. Lucchesi
*Assistant Examiner*—Melba Bumgarner

(57) ABSTRACT

A dental device for assisting in the filling and curing of a dental restoration with light activated materials having a truncated conical shape with a disposable insert member at its apex. The conical holding device has an opening at the base to accommodate a light guide and an opening at the apex to accommodate a disposable insert member. Each insert member has a shape tapered at one end thereof and an indicator means to monitor the depth of the restoration to the pulpal floor and to provide alignment of the preparation relative to the marginal ridge of the adjacent tooth.

13 Claims, 3 Drawing Sheets

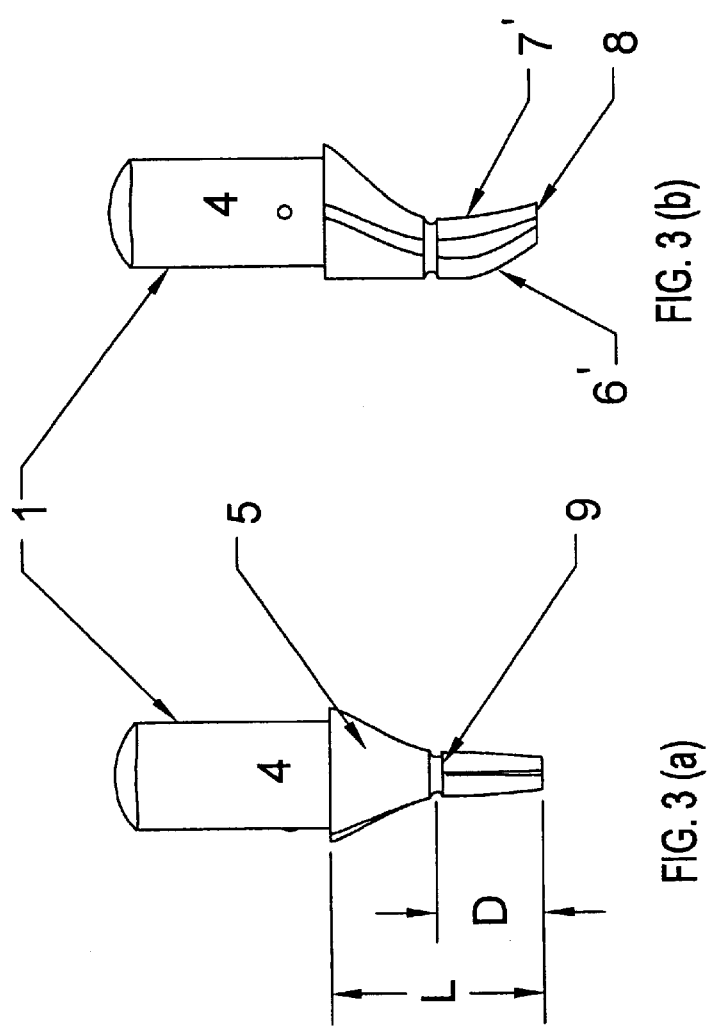
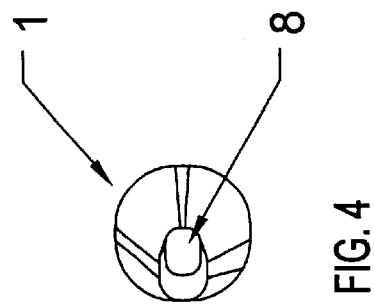

DENTAL ADAPTOR DEVICE

FIELD OF INVENTION

This invention is a continuation in part of U.S. patent application Ser. No. 09/453046, now U.S. Pat. No. 6,186, 786 filed on Dec. 2, 1999 and entitled Dental Instrument and relates to a truncated conical device that mounts on a light guide to facilitate the filling of dental cavities with light activated restorative material and more particularly to a dental device comprising an adapter of conical geometry having one end adapted to be mounted to a light guide and its opposite end adapted to be mounted to a disposable insert member for establishing proximal contact with the restorative material in a dental preparation. The dental insert member also has an indicator means for monitoring the depth of a restorative preparation and for alignment of contact the restoration with an adjacent tooth. This invention relates to a truncated conical device that mounts on a light guide to facilitate the filling of dental cavities with light activated restorative material and more particularly to a dental device consisting of a conical holding member on one end and a disposable insert member at the other end for establishing proximal contact.

BACKGROUND OF THE INVENTION

Recent advances in dentin bonding and the increased importance of esthetics in dental restorative preparations have accelerated the use of light activated resin composite materials as filling materials for both anterior and posterior restorations. However, despite improvements in materials and techniques, the placement of the resin composite remains technique sensitive and establishing firm and properly located proximal contact using resin composite filling materials particularly for posterior restorations remains difficult to achieve. If adequate contact is not achieved after matrix removal, a space will occur with the adjacent tooth. Food impaction may result in decay formation and periodontal disease. The plasticity of resin composite materials prior to the application of light radiation for curing the material makes it difficult to contour the restoration and to establish contact with adjacent teeth. In addition, it is, at present, difficult to cure composite in the deeper recesses of a dental preparation. Moreover, currently available dental devices do not make accurate contact mesially and distally to provide for adequate approximal contact during hardening and are unable to accommodate different size preparations. Commercially available devices are also unable to gauge or monitor the depth of the restoration or to assist in aligning the preparation with an adjacent tooth. For proper curing of the resin composite light must to able pass from the light curing source into the gingival floor area through the proximal box. Otherwise open margins, sensitivity and recurrent decay will develop. Accordingly, the dental device should facilitate the transmission of light into the gingival floor areas.

In our parent patent application U.S. Ser. No. 09/453046, filed on Dec. 2, 1999, the disclosure of which is herein incorporated by reference, a dental instrument of a similar nature is described except that it requires the use of a separate handle to hold the disposable light conducting insert. The device of the subject application is designed to be held in position directly on the distal end of a dental light guide which is routinely used to cure dental composite restorations. U.S. Pat. No. 4,666,405 also describes a device to position a dental light guide to cure dental composite restorations but its design does not employ a dental insert member and does not provide the ideal anatomical shape for posterior teeth nor does it provide a marginal ridge guide or an indicator to monitor the depth of the restoration to as described in this invention.

SUMMARY OF THE INVENTION

The dental device of the present invention enables light to pass deep into the proximal box and includes removable and interchangeable insert members to readily facilitate the use of the device both mesially and distally. It is adaptable for use with any size restoration by substituting different size insert members. Moreover, the insert members are disposable. Each insert member includes an indicator to monitor the depth of the restoration to the pulpal floor and to assist in alignment of the restorative preparation to the marginal ridge of an adjacent tooth.

The dental device of the present invention assists in the filling and curing of a dental restoration with light activated resin composite material(s) and comprises: a conical shaped adapter and an insert member. The adapter includes an opening for mounting a light guide at one end thereof with the opposite end having an opening to receive the insert member to establish proximal contact with restorative material in a dental preparation. The disposable insert member is removable and disposable and can be used to facilitate mesial or distal contact with the adjacent tooth.

The conical shaped adapter is wider in diameter at the end for mounting the light guide then that of the opposite end which terminates in an apex. The insert member has a shaped lower body with a lower end section which tapers downwardly for condensing restorative filling material and an upper end section which fits into the apex end of the conical adapter. The upper end section of the insert member is generally of cylindrical configuration adapted to be slidably inserted into an opening in the apex of the conical adapter. The lower end section is shaped to provide a concave surface on one side thereof and a convex surface on the opposite side and tapers downwardly to form a tip which is flat ended in cross section and of approximately rectangular geometry. The insert member further comprises indicator means to monitor the depth of the restoration to the pulpal floor and to provide alignment of the preparation relative to the height of the marginal ridge of an adjacent tooth. The insert member is preferably both removable and disposable and can be used to facilitate mesial or distal contact with the adjacent tooth.

BRIEF DESCRIPTION OF THE DRAWINGS

Other objects and advantages of the present invention will become apparent from the following detailed description of the present invention when read in conjunction with the accompanying drawings of which:

FIG. 3(a) is a front view of the insert member 1 of FIG. 1;

FIG. 3(b) is a side view of the insert member 1 of FIG. 1; and

FIG. 4 is an end view of the insert member 1 of FIG. 1.

DETAILED DESCRIPTION OF A PREFERRED EMBODIMENT

The dental device of the present invention includes a conical adapter with an insert member as shown in FIGS. 1(a)–(c) through FIGS. 3(a)–(b). Each insert member 1 is adapted to be removably mounted in the conical adapter 2.

The conical adapter 2 has a base end attached to a light guide 3 and an apex end into which is inserted a removable insert member 1. The shape of the insert member 1 can be changed by substituting a different insert member 1 with a different shape to establish a desired mesial and/or distal contact with adjacent teeth.

Figure 1:
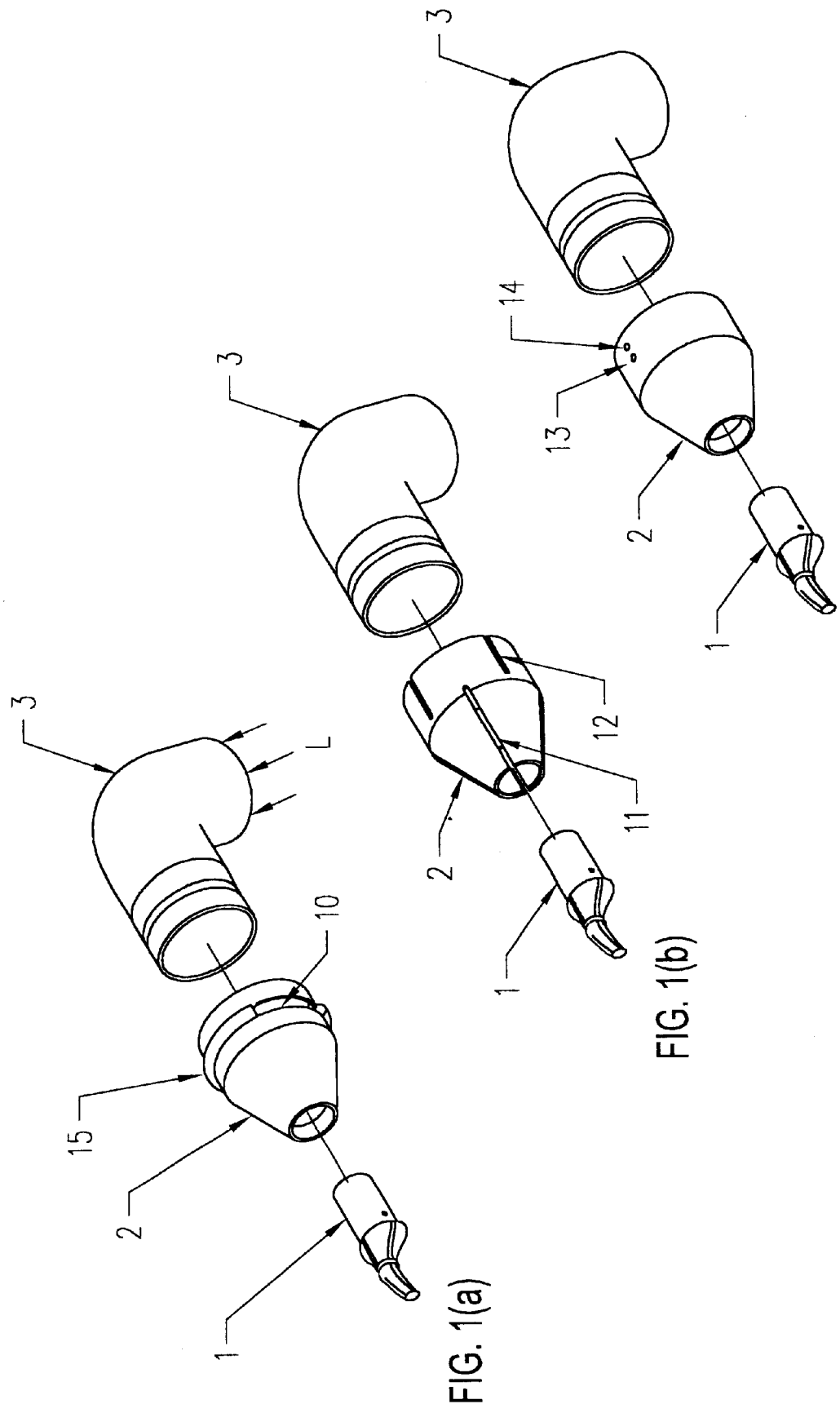
FIGS. 1(a), 1(b) and 1(c) are exploded views of different adaptor configurations of the dental adapter device of the present invention showing an insert member 1 adapted to be inserted into an opening of a conical adapter 2 which in turn has its base adapted to be inserted onto a dental light guide 3.
Figure 2:
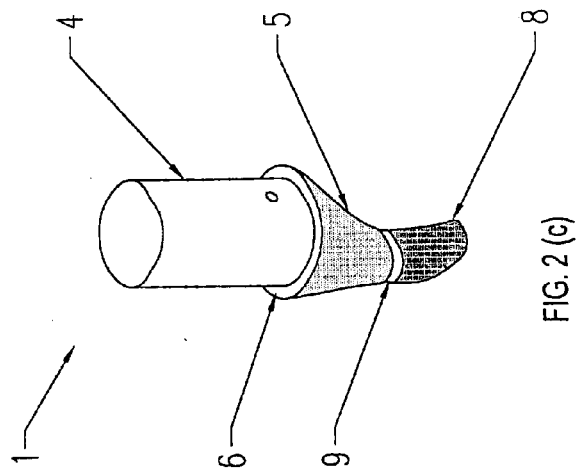
FIGS. 2(a), 2(b) and 2(c) are perspective views of the insert member 1 of FIGS. 1(a), 1(b) and 1(c) respectively with FIGS. 2(b) and 2(c) showing the insert member 1 with different textures on its lower section 5.
Figure 2:
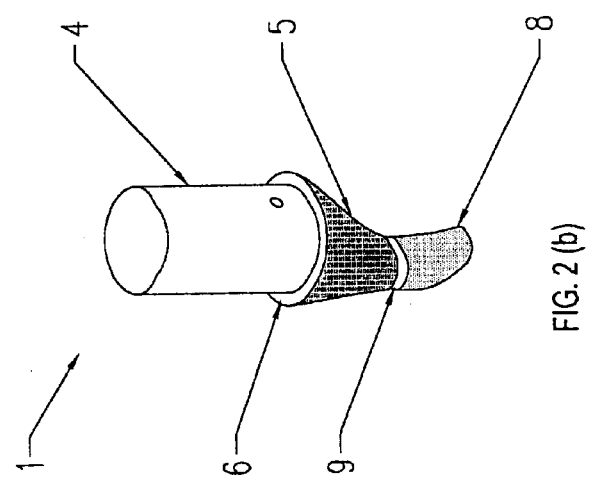
Figure 2:
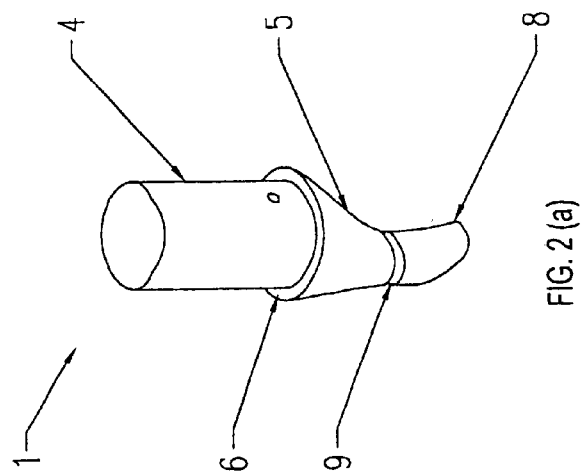

Each insert member 1 is preferably of a transparent plastic composition having a predetermined optical transmissivity. However, different insert members 1 may be composed of materials of different optical transmissivities to control the speed and degree of polymerization of the dental filling material in the restoration. Since it is known in the literature that high initial curing energy can cause material shrinkage, the transmissivity characteristic of the insert member can thus be used to control material shrinkage and strain in the restoration. The selected insert member as more clearly shown in FIGS. 2, 3 and 4 have an upper end section 4 so that it may be interchangeably mounted in the opening apex end of the adapter. Moreover, the upper end section 4 of each insert member 1 is sized and shaped commensurate with the size and shape of the opening in the apex end of the conical adapter to establish a friction fit in the apex opening when the insert member 1 is slidably inserted therein but which otherwise permits each insert member 1 to be removed therefrom. The insert member 1 also has a lower end section 5 which may be similar in shape to one another and of different textures. However, each insert member 1 may be of a different length and width so as to fit into an existing preparation and may have different shapes to accommodate pre-molar, molar and deciduous teeth.

FIG. 1(a) shows a conical adaptor 2 which has two or more slits 10 in its side. The slits allow an elastomeric "O" ring 15 to be captured in two or more places so that a portion of the "O" ring 15 projects slightly inside the clinical adaptor 2. This arrangement provides for a gripping action by the "O" ring 15 so that the adaptor 2 is held in place on a light guide 3, and can still be removed as required. FIG. 1(b) shows a conical adaptor 2 which has two or more slits 11 and 12 positioned around its circumference. These slits allow the metal of adaptor 2 to deform so that it can removeably hold insert 1 at its apex and a light guide 3 at its opposite end. FIG. 1(c) shows a conical adaptor 2 which has two or more dimples 13 and 14 on its circumference. One dimple 13 is used to hold adaptor 2 in position. The other dimple 14 provides for anti-rotation of conical adaptor 2.

The upper end section 4 of each insert member 1 and the geometry of the opening in the conical adapters is preferably cylindrical although other geometries such as a square geometry may be used. A somewhat cylindrical geometry permits the insert member 1 to be rotated in the opening of the conical adapter to accommodate mesial or distal contact and remain in a fixed position. The diameter of the cylindrical upper section 4 should be slightly smaller than the diameter of the lower section 5 at the junction adjoining the two sections 4 and 5 respectively so as to form a ledge 6 which will abut the distal end of each of the end sections upon mounting the insert member 4 into the adapter 3, shown on FIG. 1. The lower end section 5 of each insert member 1 is shaped to form a convex surface 6 on one side thereof and a concave surface 7 on the opposite side thereof as shown in FIG. 3(b). The lower end section 5 of each insert member 1 also tapers downwardly from the ledge 6 with the convex and concave surfaces 6 and 7 gradually decreasing in diameter to converge into a flat ended tip 8 of substantially rectangular configuration at the distal end thereof as shown in FIG. 4. The flat ended tip 8 is sized to provide access into a prepared tooth for condensing the filling material and permits light curing at the gingival terminus. The lower end section 5 of each insert member 1 has a marking 9, preferably represented by a circumferential groove, which is substantially horizontal and parallel to the flat ended tip 8 at a predetermined height "D" relative to the length "L" of the lower end section 5 of insert 1. The marking or groove 9 functions as a visual indicator for monitoring the depth of the restoration to the pulpal floor and used to assist in the alignment of the restoration both in height and position with the marginal ridge of an adjacent tooth. Height "D" will vary between 2 mm and 6 mm depending on the depth of the preparation. Accordingly, the marking 9 can be represented by any form of molded visual indicator including a printed marking. The greatest height of curvature is approximately 1 mm below the groove. The outer periphery of the lower end section 5 may be textured to provide the function of a mechanical lock for subsequently placed composite material. A textured surface on lower section 5 can also be used to disperse light circumferentially or selectively throughout the depth of the restoration, as shown in FIG. 2(b) and FIG. 2(c). The coarse texture permits more light to exit circumferentially and a fine texture permits less light to exit circumferentially. A gradually increasing or decreasing texture will permit a selective distribution of light. Since we know that polymerization shrinkage of the light cured resin is affected by the light intensity. This feature is important and has not been addressed in the prior art.

What is claimed is:

1. A dental device for assisting in the filling and curing of a dental restoration with light activated restorative material comprising: an adapter and a removable insert member having an upper end section and a lower end section with the lower end section having a contoured geometry with a concave surface on one side thereof and a convex surface on the side opposite thereof for establishing proximal contact with a dental preparation so that the anatomical shape of a proximal surface of a tooth being filled with said light activated restorative material can be duplicated, said adapter having a base section at one end thereof adapted to be mounted to the distal end of a light guide and having an apex at the opposite end thereof adapted to receive the upper end section of said insert member.

2. A dental device as claimed in claim 1 wherein the shaped lower end section of said insert member is mounted in substantially concentric relationship with a light activated restorative material in a dental preparation.

3. A dental device as claimed in claim 2 wherein said adapter is of conical geometry with said base section of a diameter to accommodate a light guide and wherein said apex has an opening of a diameter smaller than the diameter of said base section to accommodate the upper end section of said insert member.

4. A dental device as claimed in claim 3 wherein the upper end section of said insert member is generally cylindrical in geometry and of a diameter to fit into said opening in said apex section of said adapter.

5. A dental device as claimed in claim 4 wherein the lower end section of said insert member includes a downwardly tapered end forming a substantially flat ended tip for condensing filler material.

6. A dental device as claimed in claim 5 wherein said tip is of a rectangular shape in cross section.

7. A dental device as claimed in claim 5 wherein said insert member further includes indicator means to monitor the depth of the restoration to the pulpal floor and to provide alignment of the preparation relative to the marginal ridge of an adjacent tooth.

8. A dental device as claimed in claim 7 wherein different insert members having substantially identical upper sections and different shaped lower sections may be substituted for one another in said dental device for facilitating mesial and distal contact with an adjacent tooth.

9. A dental device as defined in claim 8 wherein each insert member has a different optical transmissivity.

10. A dental device as defined in claim 8 wherein each insert member has a textured surface to disperse light circumferentially or selectively throughout the depth of the restoration.

11. A dental device as defined in claim 7 wherein the diameter of the upper end section is smaller than the circumference of the lower end section.

12. A dental device as defined in claim 7 wherein said indicator means comprises a horizontal groove lying substantially parallel to the flat ended tip.

13. A dental device as defined in claim 3 wherein said adapter has a plurality of outer longitudinal slits extending from the distal end of said apex section toward the base section.

* * * * *